(12) United States Patent
Sahni

(10) Patent No.: US 9,125,676 B2
(45) Date of Patent: Sep. 8, 2015

(54) IMAGE GUIDED WHOLE BODY STEREOTACTIC NEEDLE PLACEMENT DEVICE WITH FALLING ARC

(76) Inventor: Hirdesh Sahni, Pune (IN)

( * ) Notice: Subject to any disclaimer, the term of this patent is extended or adjusted under 35 U.S.C. 154(b) by 1424 days.

(21) Appl. No.: 12/446,578

(22) PCT Filed: Oct. 22, 2007

(86) PCT No.: PCT/IN2007/000502
§ 371 (c)(1),
(2), (4) Date: Oct. 12, 2010

(87) PCT Pub. No.: WO2008/062474
PCT Pub. Date: May 29, 2008

(65) Prior Publication Data
US 2011/0190787 A1    Aug. 4, 2011

(30) Foreign Application Priority Data

Oct. 23, 2006    (IN) .......................... 1756/MUM/2006

(51) Int. Cl.
*A61B 19/00*    (2006.01)
*A61B 17/34*    (2006.01)

(52) U.S. Cl.
CPC ....... *A61B 19/201* (2013.01); *A61B 2017/3407* (2013.01); *A61B 2019/507* (2013.01); *A61B 2019/5236* (2013.01); *A61B 2019/5238* (2013.01); *A61B 2019/5287* (2013.01); *A61B 2019/5454* (2013.01); *A61B 2019/5466* (2013.01)

(58) Field of Classification Search
CPC ..................... A61B 19/201; A61B 2017/3407; A61B 2019/507; A61B 2019/5466; A61B 2019/5238; A61B 2019/5287; A61B 2019/5454; A61B 2019/5236
USPC .......................................... 606/130; 600/427
See application file for complete search history.

(56) References Cited

U.S. PATENT DOCUMENTS

| | | | |
|---|---|---|---|
| 4,228,799 A * | 10/1980 | Anichkov et al. | 606/130 |
| 6,989,015 B2 * | 1/2006 | Daum et al. | 606/130 |
| 2005/0033315 A1 * | 2/2005 | Hankins | 606/129 |
| 2006/0100501 A1 * | 5/2006 | Berkelman et al. | 600/415 |
| 2008/0082108 A1 * | 4/2008 | Skakoon et al. | 606/130 |

* cited by examiner

*Primary Examiner* — Katrina Stransky

(57) ABSTRACT

The subject invention is an image guided, Computerized Tomography and Magnetic Resonance Imaging compatible device for inserting needle or any such medical device at a desired place in the body.

The subject invention comprises a circular base plate, a supporting ring that is placed in a groove in the base plate, an arc, a needle guide that slides on the arc, a screw which fixes the arc with the supporting ring and the circular base plate and a locking pin which fixes the arc with the supporting ring in such a way that the arc becomes perpendicular to the circular base plate. When the locking pin is removed, this allows the arc to fall and thus frees the needle placed to move with breathing without hindrance from the subject invention, enabling placement of needle also in body parts that move with breathing.

1 Claim, 10 Drawing Sheets

IMAGE GUIDED WHOLE BODY STEREOTACTIC NEEDLE PLACEMENT DEVICE WITH FALLING ARC

FIELD OF INVENTION

This invention relates to an image guided whole body stereotactic needle placement device. More particularly it relates to a CT (computerized tomography) and Magnetic Resonance Imaging (MRI) compatible image guided stereo tactic device useful for inserting needles or any such apparatus through the said needle at a desired precise location in the human/animal body. The said needle could be used for extracting tissue/body fluid samples/delivering energy to ablate tissues etc.

BACKGROUND OF INVENTION

In medical field it is very often necessary to precisely position a medical device through a needle tip at a particular part of the body or an organ deep inside the body. This is required for obtaining tissue samples or for delivering drugs or for therapeutic/palliative aspiration of fluid collections or any such procedure.

This can be done percutaneously under image guidance obtained from cross sectional imaging devices such as ultrasound/CT scan/MRI scan etc. Image guidance is required to select least harmful path for the needle, so as to avoid vital organs and structures such as blood vessels, bowel etc. The needle can be placed free hand at an approximately correct angle by trial and error. This can also be better done by using needle guiding devices that can guide the needle in the precise direction so as to reach the precise point in the body.

These difficult and critical at time life saving operations/procedures require precise placement of needle/medical devices at precise points or locations in the body while avoiding damage to other delicate organs, tissues, blood vessels etc. Although it is possible to determine exact location using various electronic, sonic or other techniques, guiding the needles to that precise point by free hand is by trial and error and often requires multiple attempts. At times despite multiple attempts it may not be possible to place the needle or such medical device in the desired precise point in the body. At times multiple attempts of passing the needle may cause serious life threatening complications of internal bleeding and/or damage to vital organs in the path of the needle or such device.

There are devices available for guiding the needle in a precise direction under ultrasound guidance. There are also devices available for guiding the needle for brain interventions through drilled holes in the skull. However devices available for guiding the needle for brain interventions are not suitable/compatible for use in other parts of the body.

In the modern era of technology various advanced techniques such as CT and MR scanning are available for precise identification of locations needing treatment through placement of needles/medical devices through the needles or for obtaining tissue samples/body fluids. However a universal device capable of using these imaging techniques for precise placement of needles/medical devices through the needles any where in the body is not presently known and hence there is a need to develop such device.

The only reference available in respect of stereo tactic device in medical field is that of a device used for brain surgery/interventions that I could come across is titled frame for stereotactic surgery. The said device is described in U.S. Pat. No. 4,706,665 to Kasim I Gouda dated 17 Nov. 1987. The device provided by the abovementioned U.S. patent cannot be used on any other part of the body as it has been designed for brain surgery/interventions only.

The main object of the present invention is to provide an image guided stereo tactic device for needle/medical device placement that could be used for interventions in the entire of the body including brain.

Another object is to provide the said device which is compatible with both CT and MRI scan techniques and environment.

None of the existing stereotactic biopsy devices are capable of being used in body part affected by respiratory movement. In order to prevent damage to body organs and tissues in the path of the needle during respiratory movements it is mandatory to allow free movement of the needle or such device during breathing.

The present invention provides a stereotactic device that obviates the above limitations by allowing the parts used to support the needle to fall away from the needle, once the needle is placed in side the body.

In particular aspect of the present invention the device comprises a base plate at the bottom of the device with a supporting ring that fits in the base plate, an arc for needle guide, a screw and a pin to fix the supporting ring and arc and a needle guide.

DETAILED DESCRIPTION OF THE DRAWINGS

Figure 1:
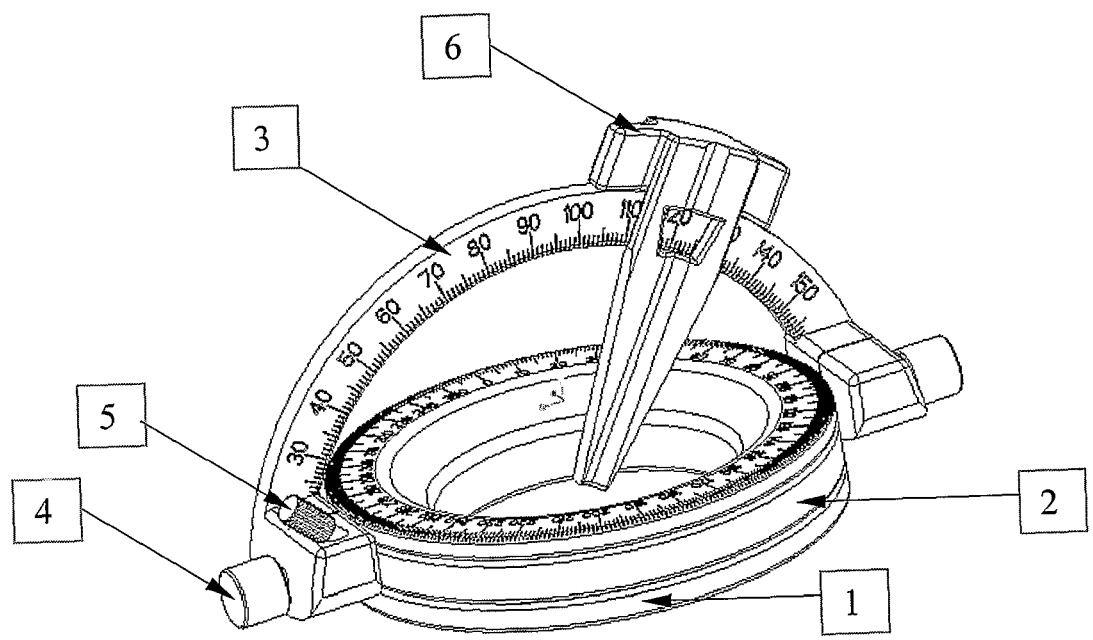
FIG. 1 Illustrates a proportional three dimensional view of the device illustrating the main components in working position.
Figure 2:
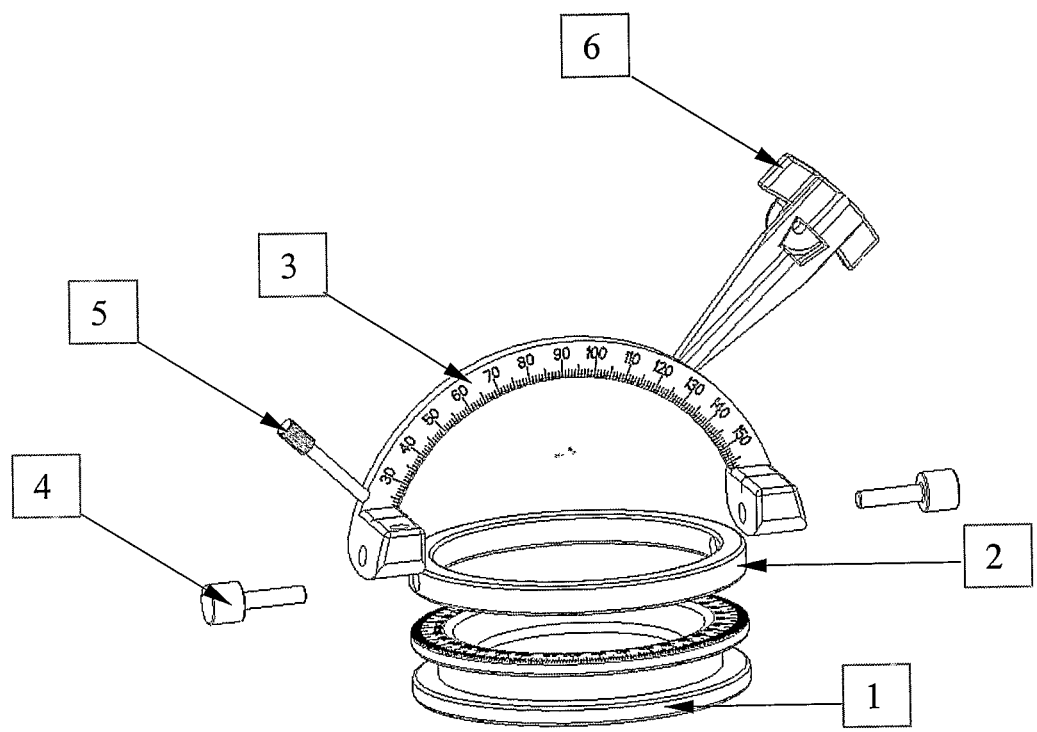
FIG. 2 shows an exploded proportional three dimensional view of the device illustrating the main components.
Figure 3:
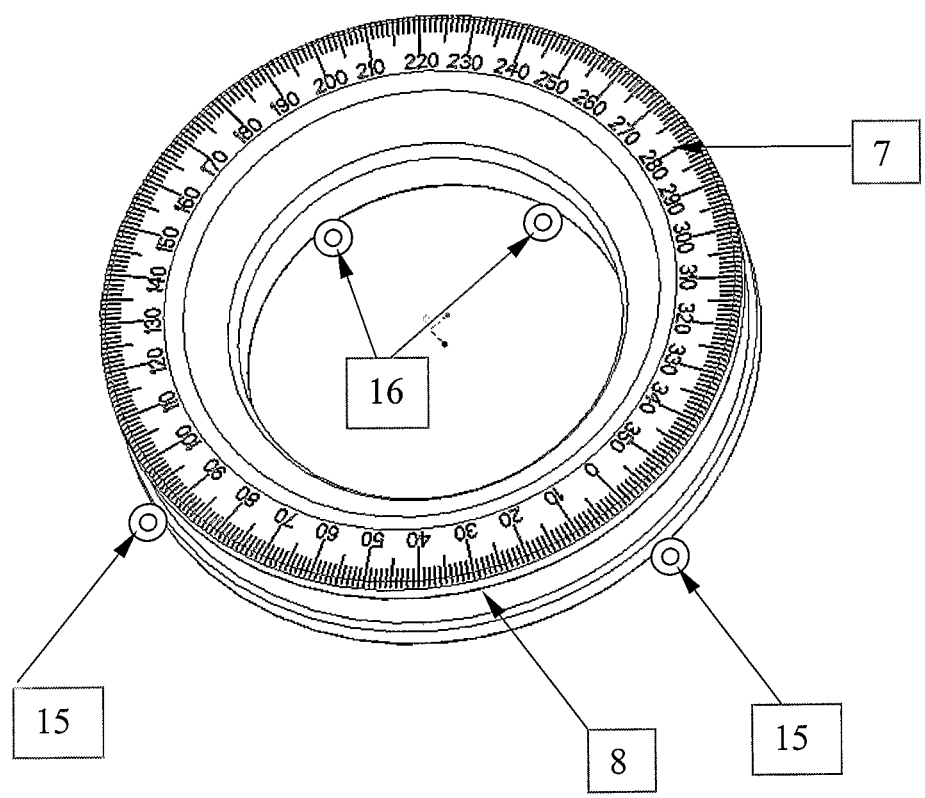
FIG. 3 Shows angled three dimensional top view of the base plate.
Figure 4:
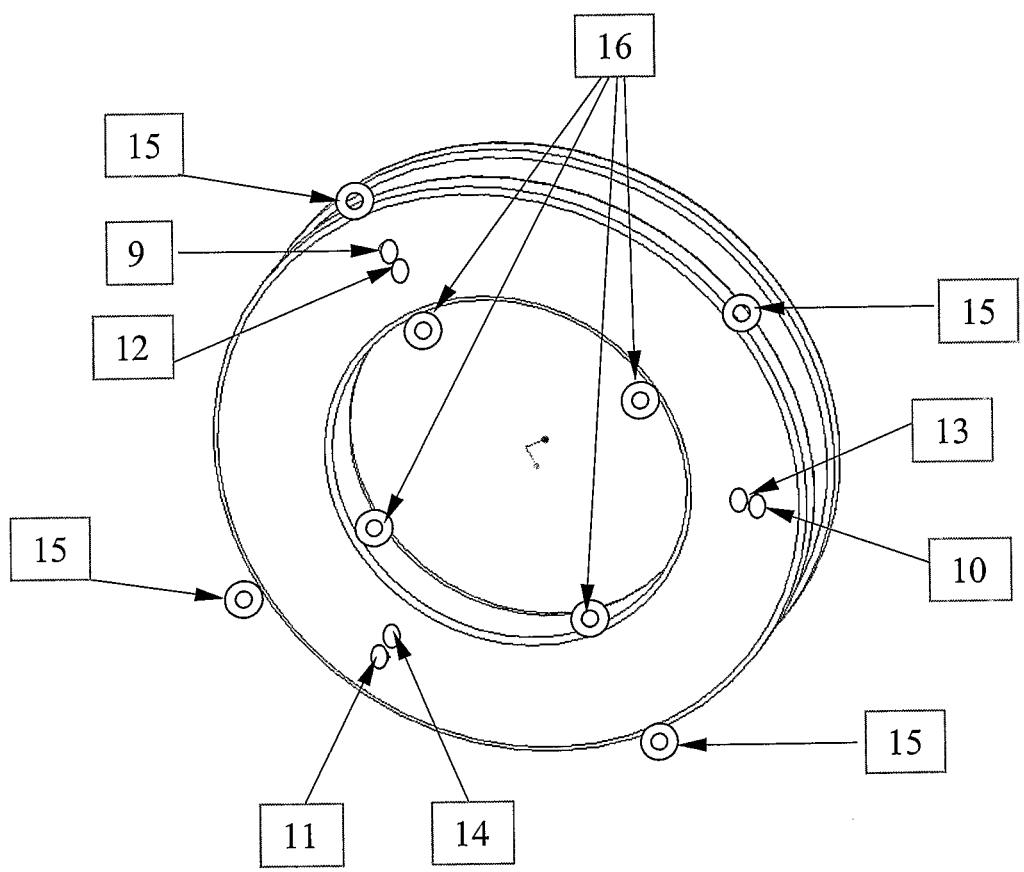
FIG. 4 Shows angled three dimensional bottom view of the base plate.
Figure 5:
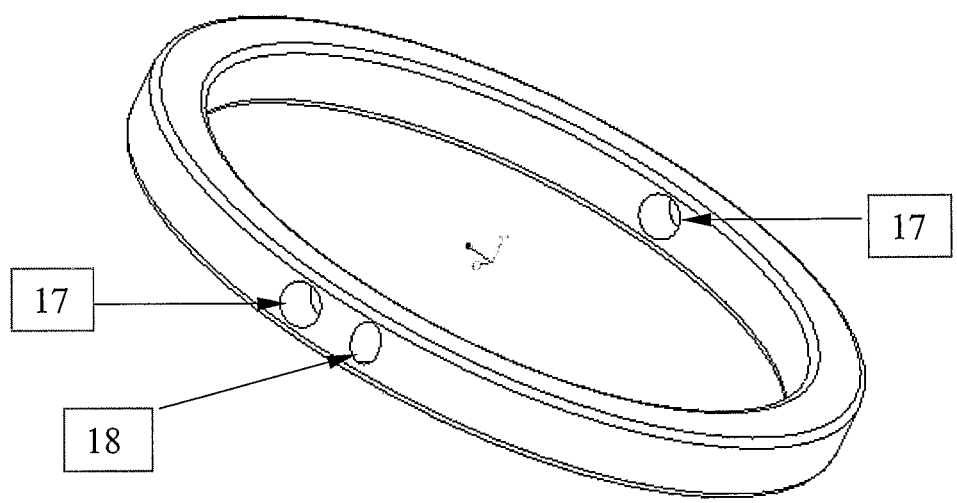
FIG. 5 Shows the angled three dimensional view of supporting ring.
Figure 6:
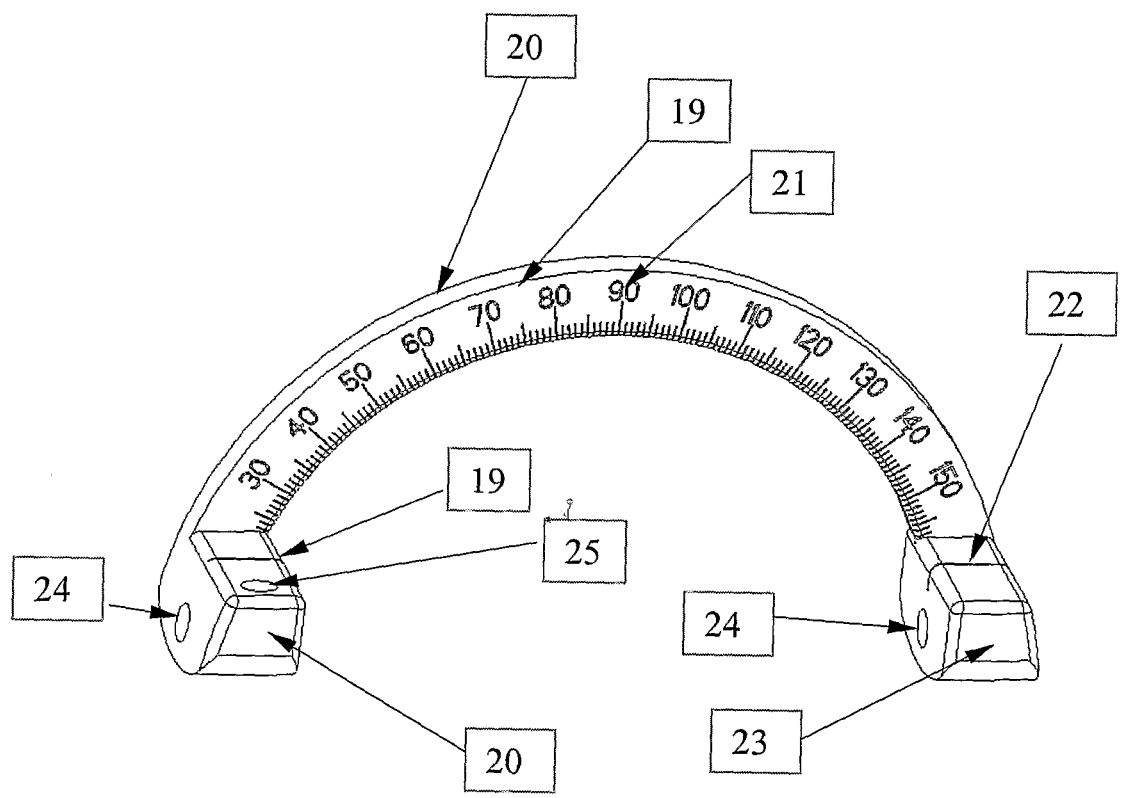
FIG. 6 Shows the angled three dimensional front view of the carrying arc for needle guide.
Figure 7:
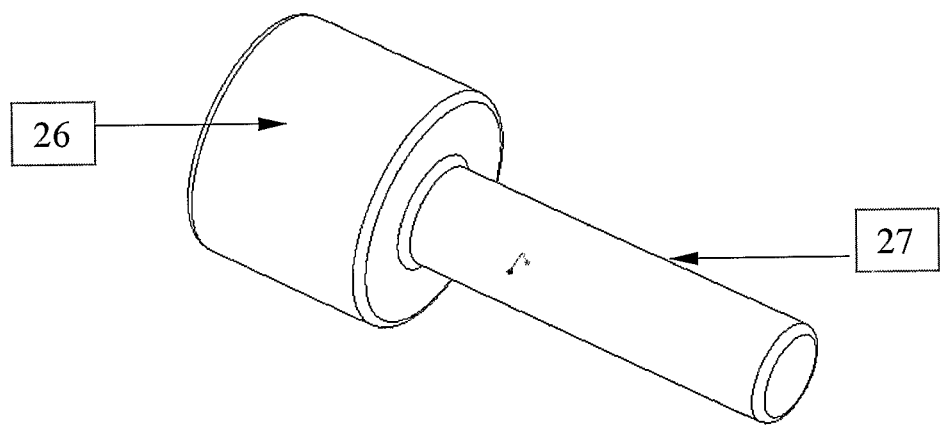
FIG. 7 Shows the angled three dimensional side view of fixing screw.
Figure 8:
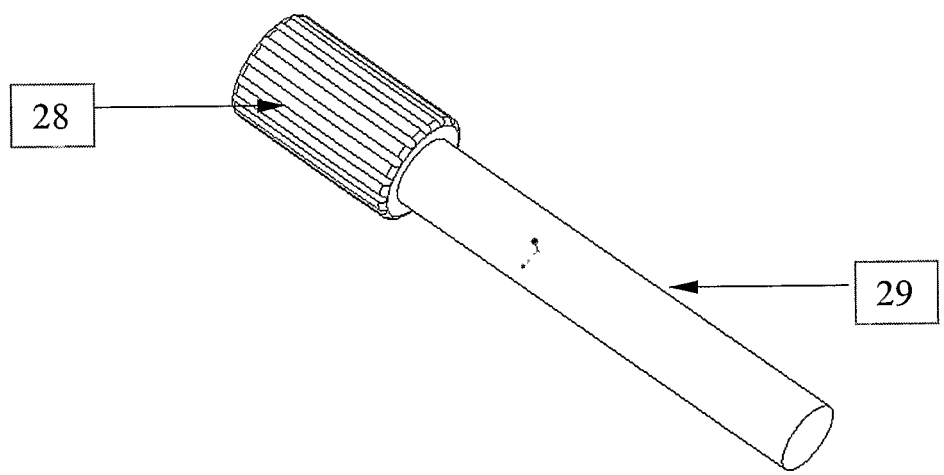
FIG. 8 Shows the angled three dimensional side view of the locking pin.
Figure 9:
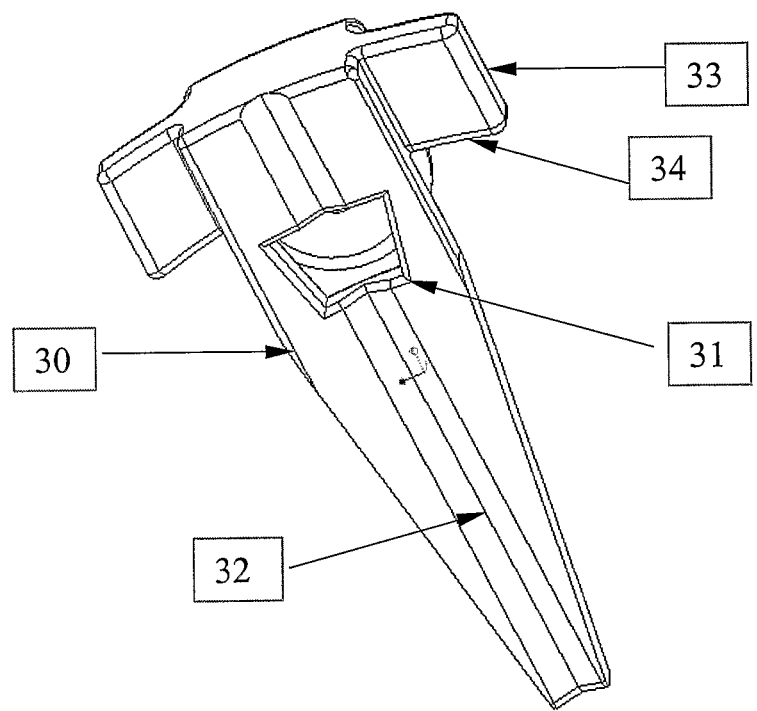
FIG. 9 Shows the angled three dimensional front view of the needle guide.
Figure 10:
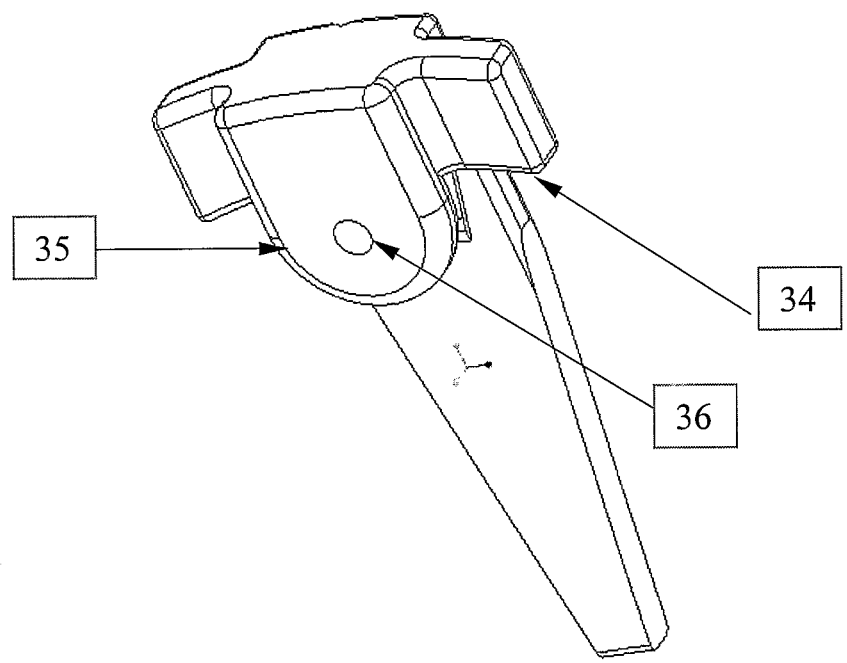
FIG. 10 shows the three dimensional side back view of the needle guide.

Referring more particularly to the drawings, FIG. (1) Illustrates various components of the device of the present invention in three dimensional perspective, the device comprising a circular base plate (1), a circular supporting ring (2) that is placed in the groove in base plate for supporting ring (8), a carrying arc for needle guide (3) which has a foot on either side (23), a fixing screw (4) which fixes the carrying arc for the needle guide (3) with the supporting ring (2) and the base plate (1), a locking pin (5) which fixes the carrying arc for needle guide (3) with the supporting ring (2) making the carrying arc for the needle guide (3) perpendicular to the base plate (1) and a needle guide (6) that slides on the superior surface of the carrying arc for the needle (20).

FIG. (2) Shows an exploded view of the complete device comprising of the base plate (1), supporting ring (2), carrying arc for needle guide (3), fixing screw (4), locking pin (5) and needle guide (6).

FIG. (3) Shows angled three dimensional top view of the base plate (1), which is ring shaped and has radial markings in degrees on the top surface (7), and has a circular grove for the supporting ring (8) on its side. It also has an outer (15) and an inner (16) set of rings for securing the base plate to the patient. These are at 0, 90, 180 and 270 degrees.

FIG. (4) Shows the angled three dimensional bottom view of the base plate (1) showing six fiducial markers in all. These are in sets of two adjoining markers. The outer of these two being MR visible and the inner being CT visible. The markers in each set are along the radius. These sets of fiducial markers are placed at 120 degrees from the adjoining sets. Each set is labeled central, left or right. The central marker is at 0 degrees, the left is at 120 degrees and the right is at 240 degrees radial. These degrees are as marked on the top surface of the base plate (7). The central outer marker (9), the left outer marker (10) and the right inner marker (11) are are visible on Magnetic resonance imaging (MRI) and are at 0, 120, 240 degrees respectively. The central inner marker (12), the left inner marker (13) and the right inner marker (14) are radio-opaque, MR compatible and are visible on Computerised Tomography (CT) and on X-Ray fluoroscopy, and are at 0, 120, 240 degrees respectively. The MR visible fiducial markers are equidistant from the centre of base plate. The CT visible fiducial markers are equidistant from the centre of base plate. These fiducial markers are useful for localizing the base plate (1) in the co-ordinates system of the cross sectional imaging device such as CT/MRI FIG. (5) Shows the three dimensional view of the supporting Ring (2) which is ring shaped and has two end to end tapped holes (17) that are diametrically opposite to each other. These allow the stem (27) of the fixing screw (4) to get fixed in the groove on the base plate (8). There is another hole (18) which is for the stem of locking pin (29).

FIG. (6) Shows three dimensional front view of the carrying arc for needle guide (3), having an arc blade (19) and a foot on either side (23). The arc has a superior surface (20) that is concentric with fiducial markers (9-14) and the base plate (1). The arc blade has radial markings in degrees on its front surface (21). The foot of arc (23) have a linear mark (22) on upper surface, and hole (24) one on each side for stem of fixing screw (27). The right foot of the arc has an oblique hole (25) for stem of locking pin (29).

FIG. (7) Shows the angled three dimensional side view of Fixing Screw (3) comprising of a grip (26) and a stem (27). This screw fixes the supporting ring (2) and the carrying arc for needle guide (3) to the base plate (1) at a desired radial marking in degrees on the top surface of the base plate (7).

FIG. (8) Shows the angled three dimensional side view of locking pin (5) comprising of a grip (28) and a stem (29). The stem of locking pin (29) passes through the hole in foot of arc (24) and the taped hole in supporting ring (17). This locking pin fixes the carrying arc for needle guide (3) perpendicular to the base plate (1).

FIG. (9) Shows angled three dimensional front view of needle guide, comprising of a head (33), a front plate (30) and a back plate (35). The head has an inferior surface (34) that is concentric to the superior surface of the arc blade (19). The front plate (30) has a window (31) through which the radial markings in degrees on the front surface of the arc blade (21) are visible. There is also a wedge shaped needle track (32) on the front plate of the needle guide (30).

FIG. (10) Shows angled three dimensional back view of needle guide (6), showing the back plate (35). The back plate of needle guide has a tapped hole (36) for a screw to fix needle guide to the arc blade (19).

In another embodiment of the present invention the material of making various components has no limitations and these could be made of any suitable material such as metal, polymer etc used in the art provided it is CT and/or MR Compatible.

The whole body stereotactic needle placement device provided by the present invention may be used for any part of the human body from where the sample is to be taken for diagnosis or drugs are to be delivered or fluids are to be aspirated for diagnosis or treatment. The CT or MRI scan provides the exact location in the body where the tip of needle/medical device is to be positioned.

The CT/MRI scan of the desired part of the patient's body is performed. The desired position of the entry of the needle/medical device is determined from the obtained scans ensuring the safest pathway for the needle/medical device. The base plate (1) is secured to the patient's body by putting sutures or screws through the outer (15) and/or inner (16) set of rings on the base plate, so as to get the desired position of the entry of the needle/medical device in the centre of the base plate (1).

The CT/MRI scan of the desired part of the patient's body is performed once again. The x, y, z coordinates of the fiducial markers (9), (10) and (11) for MR and (12), (13) and (14) for CT, and of the desired position of the needle tip/medical device in the patient's body (target) are obtained from the software provided in the CT/MRI scanner. These x, y, z coordinates of the fiducial markers and the target are fed to mathematical software specifically designed for this device. This software calculates the angle at which the carrying arc for needle guide (3) has to be placed on the base plate (1); angle at which the needle guide (6) has to be placed on the Arc blade (19) and the depth of the target from the skin at the centre of base plate to the target. These angles and the depth of the target can be alternatively obtained with the help of a specifically designed 3D frame, in which the coordinates are manually adjusted. The software and the frame have not been included in this patent.

The wedge shaped needle track (32), points in the exact direction of the target from the desired site of the entry of the needle/medical device the body of the patient, once the carrying arc for needle guide (3) is fixed on the base plate (1) and the needle guide (6) is fixed on the superior surface of arc blade (20) at precise degree markings on the arc blade (21) and radial markings on the base plate (7), obtained by feeding the x, y, z co-ordinates of the fiducial markers (9), (10) and (11) for MR and (12), (13) and (14) for CT, and the target in the software or the 3D frame. Once the position of the Carrying arc for needle guide (3) and the needle guide (6) is adjusted these can be secured by placing fixing screw (4) in the hole in foot of carrying arc (24) and a screw in tapped hole in back plate of needle guide (36).

A small incision appropriate to the diameter of the needle/medical device to be placed in the patient's body is made at the desired point of entry in the skin. The needle/medical device is advanced to the calculated depth. In case the part of the body where this device is used moves with breathing, it is ensured that the patient is holding breath during passage of needle/medical device. The needle is made free by removing the locking pin (5), and thus allowing the carrying arc (3) to fall, before asking the patient to breath again.

Once the needle/medical device tip has been positioned at the desired location in the patient's body it can be used to take samples, deliver the medication or aspirate fluids or to perform any such procedure.

The image guided whole body stereotactic needle placement device with falling arc, provided by the present invention has following advantages:
1. It enables precise placement of needle in any desired location in the body, including brain, chest and abdomen.
2. It can be used in patients of any age, including infants.
3. Positioning of the needle could also be done in directions other than the axial plane of the body.
4. The device virtually eliminates multiple attempts to place the needle in desired location along the desired path.
5. It minimizes the morbidity and mortality of the procedure.
6. It increases the success rate of the procedure being performed.
7. It is both CT and MR compatible.

I claim:

1. An image guided whole body stereotactic needle placement device with falling arc for placement on a patient comprising:
- a circular base plate comprising a circular groove and an outer and an inner set of rings for securing the base plate to the patient, a bottom surface of the base plate comprising six fiducial markers, in sets of two, one of these being magnetic resonance imaging visible and the other being computerized tomography visible, the markers in each set are located along the radius, at 120 degrees from the adjoining sets; at 0 degrees, 120 degrees and at 240 degrees on a top surface of the base plate;
- a circular supporting ring being placed in the circular groove of the base plate, the circular supporting ring comprises two end to end tapped holes that are diametrically opposite to each other, and the circular supporting ring having an obliquely placed blind hole;
- a fixing screw having a grip and a stem, the fixing screw fixes the circular supporting ring, and the carrying arc to the base plate at a desired radial marking in degrees on the top surface of the base plate;
- a carrying arc for a needle guide, being fitted to the circular supporting ring, the carrying arc comprising an arc blade, a left foot and a right foot on the carrying arc, the carrying arc further comprising a superior surface that is concentric with the fiducial markers, at least one of either the right foot or the left foot of the carrying arc having an oblique hole in alignment with the oblique hole of the circular supporting ring; and at least one of the either right foot or the left foot having another hole adapted to receive the stem of the fixing screw;
- a locking pin for fixing the carrying arc to the circular supporting ring and making the carrying arc perpendicular to the base plate, the locking pin comprising a grip and a stem, the stem of the locking pin passing through at least one of the oblique holes in the right foot or the left foot of the carrying arc;
- a needle guide being able to slide over the superior surface of the carrying arc, the needle guide comprises a head, a front plate and a back plate, where the head has an inferior surface that is concentric to the superior surface of the arc blade, and the front plate has a window through which the radial markings in degrees on the front surface of the arc blade are visible, and a wedge shaped needle track on the front plate of the needle guide, and the back plate of the needle guide having a tapped hole for inserting a screw to fix the needle guide to the arc blade.

* * * * *